United States Patent [19]

Godfrey

[11] Patent Number: 5,250,569
[45] Date of Patent: Oct. 5, 1993

[54] AMINO ACID FLAVORINGS OF ALUMINUM ASTRINGENT FOR ORAL USE

[75] Inventor: John C. Godfrey, Huntingdon Valley, Pa.

[73] Assignee: Godfrey Science & Design, Inc., Huntingdon, Pa.

[21] Appl. No.: 688,318

[22] Filed: Apr. 22, 1991

[51] Int. Cl.$^5$ .................... A01N 37/12; A01N 37/44; A61K 31/195

[52] U.S. Cl. .................... 514/561; 424/440; 424/465; 424/468

[58] Field of Search ............ 424/440, 468, 465, 682, 424/684, 49, 52; 514/553, 974, 561

[56] References Cited

U.S. PATENT DOCUMENTS 2,556,567  6/1951  Wright ........................... 424/682
4,684,528  8/1987  Godfrey ......................... 426/74
4,758,439  7/1988  Godfrey ......................... 426/74

*Primary Examiner*—Marianne M. Cintins
*Assistant Examiner*—Rebecca Cook
*Attorney, Agent, or Firm*—Breiner & Breiner

[57] ABSTRACT

Formulations of aluminum compounds with select amino acids such as glycine (aminoacetic acid) in a base material are described. The base material can be a sweetening agent such as a hard or soft candy base, a syrup, chewing gum, dentifrice, or the like. The advantage of such formulations is that the unpalatable and undesirable tastes and aftertastes of unformulated aluminum compound and of aluminum compounds mixed with a base material are markedly reduced and the products may be slowly dissolved in the mouth to achieve nutritional or therapeutic results. Processes for the satisfactory preparation of the formulations are set forth.

29 Claims, No Drawings

AMINO ACID FLAVORINGS OF ALUMINUM ASTRINGENT FOR ORAL USE

Field of Invention and Background

This invention relates to astringent aluminum compounds for oral use. More particularly this invention relates to compositions containing an aluminum compound which, when taken orally, is palatable without undesirable aftertaste. These compositions include, in addition to the aluminum compound, a base material and a select amino acid.

Aluminum is the third most abundant element, after oxygen and silicon, on the surface of the earth as described in *Chemistry*, M. J. Sienko and R. A. Plane, McGraw-Hill Book Co. (1957) at page 462. The earth's crust is 8% aluminum, primarily as the oxide $Al_2O_3$ and complex aluminum silicates such as felspar, $KAlSi_3O_8$. Consequently, all extant forms of life have evolved mechanisms to cope successfully with their extensive exposure to this element in its numerous compounds, and it therefore possesses very low toxic potential to plants and animals, including man. common aluminum compounds are comparable to sodium chloride in respect to toxicity.

The value of astringent compounds of aluminum for both internal (food and medicinal) and cosmetic use has been known for more than a century. The wide use and general acceptance of aluminum compounds and preparations for a variety of food, medicinal and cosmetic purposes, and the high degree of safety of aluminum so used, is demonstrated in the following references from the medical and technical literature.

Goodman and Gilman in *The Pharmacological Basis of Therapeutics*, 5th Ed., MacMillen Pub. Co. (1975) at, p. 962, state "Aluminum hydroxide is a compound of essentially low toxicity." On p. 963 it is noted that dihydroxyaluminum aminoacetate, $Al(OH)_2H_2NCH_2CO_2$, is an antacid available under the name "Robalate." It is administered three to four times daily in doses of 0.5 to 2 grams (p. 969).

The "Merck Manual of Diagnosis and Therapy" 15th. Ed. (1987) at page 743, provides the information that "Aluminum hydroxide is [a] safe, commonly-used antacid."

Blakiston's Gould Medical Dictionary," 4th Ed. (1979) at page 55, reveals that ammonium alum, $AlNH_4(SO_4)_2.12H_2O$, and potassium alum, $AlK(SO_4)_2.12H_2O$ are used as astringents; aluminum acetate, $Al(CH_3CO_2)_3$, as a 5.3% solution in water is known as Burow's Solution which is used as a topical astringent and antiseptic, but when diluted with 10 to 40 parts of water (0.53% to 0.013% aluminum acetate) it is used as a gargle or for local application for ulcerative conditions (e.g. aphthous ulcers of the mouth; aluminum chlorhydrate, $Al(OH)_2Cl$, is an antiperspirant; aluminum hydroxide, $Al(OH)_3$, is a protective agent and astringent for ulcers; aluminum phosphate, $AlPO_4$, and aluminum silicate, $Al_2SiO_5$, are used as components of dental cements; and aluminum sulfate, $Al_2(SO_4)_3.18H_2O$, is an astringent and antiseptic.

"Dorland's Illustrated Medical Dictionary" 25th Ed. (1974) at pages 62–63 provides the information that dihydroxyaluminum aminoacetate, $Al(OH)_2H_2NCH_2CO_2$, is an antacid agent; aluminum carbonate, $Al_2(CO_3)_3$, is a styptic, (defined as an antihemorrhagic astringent, e.g. for small cuts); aluminum chloride, $AlCl_3.6H_2O$, is a local astringent with a sweet taste; aluminum hydroxide, $Al(OH)_3$, is a white, tasteless powder which is a mild astringent for internal and external use; and aluminum sulfate, $Al_2(SO_4)_3.18H_2O$, is an astringent and antiperspirant with a sweet taste.

Grollman in Pharmacology and Therapeutics, 4th Ed. (1960), affirms the safety and lack of toxicity of alum, $AlK(SO_4)2.12H_2O$, p. 963. He also reports that aluminum aminoacetate, $Al(OH)_2H_2NCH_2CO_2$, is an antacid which is administered as 0.5 gram tablets, p. 497.

The "Handbook of Non-Prescription Drugs", 6th Ed. (1979) reports that aluminum acetate, $Al(CH_3CO_2)_3$, is used widely for conditions involving the external ear because it safely lowers the local pH to an antibacterial level (p. 276). Aluminum magnesium silicate, $Al_2MgO_8Si_2$, at 8.83 mg/ml, is useful as an oral anti-diarrheal medication (p. 36).

The "Food Chemicals Codex", 1st Ed. Nat.l Acad. of Sci.-Nat.l Res. Council (1966) lists ammonium alum, $AlNH_4(SO_4)_2.12H_2O$ (p. 27), potassium alum, $AlK(SO_4)_2.12H_2O$ (p. 29), and sodium alum, $AlNa(SO_4)_2.12H_2O$ (p. 30) as buffers and neutralizing agents for use in foods; and aluminum sulfate, anhydrous and octadecahydrate, $Al_2(SO_4)_3.nH_2O$ (n=0 or 18) as a firming agent for use in foods (p. 32). For that reason the common alums and aluminum sulfate are very frequently found as ingredients in home- and commercial-pickling solutions, i.e. in dill pickles and the like.

Part 182 of the "Code of Federal Regulations" Title 21 (1987) at page 382, lists by name among the Multiple Purpose GRAS Food Substances aluminum sulfate, aluminum ammonium sulfate, aluminum potassium sulfate, and aluminum sodium sulfate; and as GRAS Anti-Caking Agents sodium aluminosilicate, sodium calcium aluminosilicate, and aluminum calcium silicate.

The foregoing citations clarify the status of aluminum compounds as safe and generally acceptable agents for various food and medical applications.

It is now known that there are instances in which the strong astringency of aluminum compounds can best be utilized for medicinal purposes within the oral cavity, e.g. in the treatment of aphthous ulcerations of the tongue, mouth, or lips, but in which such utility is greatly limited by the unpleasant taste of many of the otherwise-useful aluminum compounds. Surprisingly it has now been discovered that for those aluminum compounds which are by themselves unacceptable in taste, the addition thereto, as physical mixtures, of very modest amounts of simple amino acids produces a remarkable moderation and improvement of the flavor of the aluminum compounds, without any material alteration of their astringent properties. Furthermore, the flavors of other astringent aluminum compounds which are not entirely unacceptable by themselves are improved to a significant and useful extent by the addition thereto of small amounts of simple amino acids.

Until the present time, there has been no great interest in the discovery of aluminum salts and formulations thereof that would have acceptable taste, as they have traditionally been used only as adjuvants in food recipes, for topical application other than in the oral cavity, and for internal use as in the treatment of stomach ulcers and as antacids. It has now been discovered, however, that strong astringency in and of itself is of value in reduction of the duration of symptoms of the common cold. In a double-blind clinical study entitled "Zinc Gluconate and the Common Cold: A Controlled Clinical Study" *Antimicrobial Agents and Chemotherapy*, J. C.

Godfrey et al, (1991) (in press), a placebo which contained tannic acid and which matched the astringency of the zinc gluconate formulation being tested was found to reduce the duration of cold symptoms in wildtype colds from a mean total of 9.1 days if treatment with the placebo began after symptoms had been present for two days, to 6.5 days if treatment with the placebo began after symptoms had been present for one day or less. This difference of 2.5 days was highly significant, $p<0.01$. If the placebo used in this study had been entirely inactive, treatment with it should have resulted in the same total duration of symptoms of about 9.2 days, regardless of when such treatment started, with respect to the time of onset of symptoms, J. C. Godfrey et al, supra. Following this observation, it was discovered that symptoms of allergic rhinitis (sneezing, nasal stuffiness and postnasal drainage) are alleviated by the oral application of very small amounts of astringent aluminum salts, which is in agreement with the hypothesis put forth in, J. C. Godfrey et al, supra that a strong astringent may temporarily "clamp" the endings of the trigeminal and other nerves which are near the surface of the oral mucosa and which serve the sinus cavities as well. This chemical "clamp" appears to work very much like the physical clamp of the trigeminal nerve, i.e. finger pressure under the nose, to temporarily inhibit sneezing and rhinitis. Because of the foregoing observations, there is now good reason to discover aluminum salts and formulations thereof that would have acceptable taste, in order to take advantage of these innocuous agents as treatments to relieve upper respiratory discomfort.

Accordingly, in order to take advantage of the important effect of aluminum upon symptoms of rhinitis from a diversity of causes, it is necessary to develop a formulation or formulations of pharmaceutically acceptable salts which are palatable enough to be taken with the frequency necessary to suppress the said symptoms.

PRIMARY OBJECTS AND GENERAL DESCRIPTION OF THE INVENTION

Accordingly, it is a primary objective of this invention to provide an aluminum formulation or formulations for oral use which are palatable and do not have a disagreeable aftertaste.

This primary and other objectives of the invention will be apparent from the following general description and the detailed examples.

According to the present invention, it has been found that the compositions containing an aluminum compound, a base material such as a candy or syrup and certain amino acids in which the molar ratio of amino acid to aluminum is in the range of one to twenty are very pleasant to the taste and have no undesirable aftertaste. The amino acids which are useful for the purpose of this invention are glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,l-lysine. It has also been found that complexes between aluminum and the named amino acids having the composition Al(amino acid)$_3$ are water-soluble and have very good flavors when formulated with an excess of the same amino acid, said excess being in the range of 1 to 20 moles of the said amino acid per mole of Al(amino acid)$_3$. It has further been found that certain other amino acids such as aspartic and glutamic acids are not useful for this purpose. Therefore, it has been found that it is not possible to predict which aluminum and amino acid combination will have acceptable taste unless it is prepared and tested.

The aluminum compounds which can be used in combination with the amino acids noted above can be any of the forms commonly used such as the sulfate, chloride hexahydrate, acetate, acetotartrate, ammonium sulfate, diacetate (known also as basic aluminum acetate), hydroxychloride, magnesium silicate, potassium sulfate ("alum"), sodium sulfate ("soda alum"), acetate oxide, gluconate, glucuronate, and ascorbate, as well as complexes of trivalent aluminum with the amino acids.

The base material which can be utilized as a carrier for the aluminum compound and the select amino acid can be a sweetening agent such as a soft or hard candy base; a syrup such as corn syrup; a gum material including chewing gums, or any other form which permits the oral intake of the aluminum compound and particularly where the composition is retained in the mouth for a substantial period of time to permit prolonged contact in the mouth with the aluminum to provide a slow release of aluminum into the mouth. Preferably the base material is a hard or soft candy base optionally containing a flavoring agent such as a fruit flavor concentrate or a syrup such as a natural or artificially sweetened syrup.

The following examples will serve to illustrate, but not to limit, the present invention.

Preparation of Lemon-Flavored Hard Candy Stock

A mixture of 400 g of sucrose, 160 ml of white corn syrup, and 160 ml of deionized water was heated to 212° F. in a one-liter teflon-lined aluminum pan. When a clear solution was obtained, the mixture was heated without further stirring at the maximum rate possible without boil-over until the temperature of the mixture reached 300° F. The product was allowed to cool to 280° F. and 5 g of cornstarch to serve as a carrier for the flavoring oil was dusted on top of the cooling product. 12 ml of "Virginia Dare Lemon Extract" was added and the mixture was thoroughly blended. The pale straw-colored product was poured in a 4 mm layer onto a lightly greased heavy aluminum pan. On cooling to room temperature, the layer was fractured into convenient-sized pieces and stored in a sealed container. The yield was 523 g of product known in the art as "hard crack" caramel.

Compositions with Hard Candy Base Material

Examples 1-9 which comprise a hard candy base contain from 1 to 6 mg of aluminum per gram of the composition.

EXAMPLE 1

Lemon-Flavored Aluminum Sulfate Formulation 92.6 g of lemon-flavored hard candy stock was placed in an aluminum pan and heated at 210° F. to a mobile syrup. To this hot stock was added 7.38 g of a dry, finely-ground mixture containing 3.47 g of Al$_2$(SO$_4$)$_3$.18H$_2$O and 3.91 g of anhydrous glycine, C$_2$H$_5$NO$_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square.

On cooling to room temperature, the squares were easily broken out of the mass. The yield was 33 pieces with an average weight of 2.4 g. The aluminum content was 2.81 mg per gram and glycine content was 39.1 mg per gram. The molar ratio of glycine to aluminum was 5 to 1. The flavor was very pleasant, without unpleasant aftertaste, but with a strongly astringent and persistant mouth-feel.

A similar product containing all of the same ingredients except glycine possessed an identical astringent mouth-feel, but with a distinctly unpleasant taste and aftertaste

EXAMPLE 2

Lemon-Flavored Aluminum Sulfate Formulation 94.4 g of lemon-flavored hard candy stock was placed in an aluminum pan and heated at 210° F. to a mobile syrup. To this hot stock was added 5.65 g of a dry, finely-ground mixture containing 1.74 g of $Al_2(SO_4)_3.18H_2O$ and 3.91 g of anhydrous glycine, $C_2H_5NO_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 31 pieces with an average weight of 2.6 g. The aluminum content was 1.40 mg per gram and glycine content was 39.1 mg per gram. The molar ratio of glycine to aluminum was 10 to 1. The flavor was very pleasant, without unpleasant aftertaste. Persistent astringency was present and was noticeably less than that of the product of Example 1.

EXAMPLE 3

Lemon-Flavored Aluminum Acetate Oxide Formulation 95.1 g of lemon-flavored hard candy stock was placed in an aluminum pan and heated at 210° F. to a mobile syrup. To this hot stock was added 4.90 g of a dry, finely-ground mixture containing 0.99 g of $Al_2O(CH_3CO_2)_4.4H_2O$ and 3.91 g of anhydrous glycine, $C_2H_5NO_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 32 pieces with an average weight of 2.5 g. The aluminum content was 1.40 mg per gram and glycine content was 39.1 mg per gram. The molar ratio of glycine to aluminum was 10 to 1. The flavor was very pleasant, without unpleasant aftertaste, but with a moderately astringent and persistant mouth-feel.

EXAMPLE 4

Lemon-Flavored Aluminum Ammonium Sulfate Formulation 94.9 g of lemon-flavored hard candy stock was placed in an aluminum pan and heated at 210° F. to a mobile syrup. To this hot stock was added 5.10 g of a dry, finely-ground mixture containing 2.36 g of $AlNH_4(SO_4)_2.12H_2O$ and 2.74 g of anhydrous glycine, $C_2H_5NO_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 31 pieces with an average weight of 2.3 g. The aluminum content was 1.40 mg per gram and glycine content was 23.6 mg per gram. The molar ratio of glycine to aluminum was 7 to 1. The flavor was very pleasant, without unpleasant aftertaste, but with a strongly astringent and persistant mouth-feel.

EXAMPLE 5

Lemon-Flavored Aluminum Chloride Formulation 92.34 g of lemon-flavored hard candy stock was placed in an aluminum pan and heated at 210° F. to a mobile syrup. To this hot stock was added 7.66 g of a dry, finely-ground mixture containing 1.62 g of $AlCl_3.6H_2O$ and 6.04 g of anhydrous glycine, $C_2H_5NO_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 36 pieces with an average weight of 2.4 g. The aluminum content was 1.81 mg per gram and glycine content was 60.4 mg per gram. The molar ratio of glycine to aluminum was 12 to 1. The flavor was very pleasant, without unpleasant aftertaste, but with a strongly astringent and persistant mouth-feel.

EXAMPLE 6

Lemon-Flavored Aluminum Potassium Sulfate Formulation 90.09 g of lemon-flavored hard candy stock was placed in an aluminum pan and heated at 210° F. to a mobile syrup. To this hot stock was added 9.91 g of a dry, finely-ground mixture containing 3.96 g of $AlK(SO_4)_2.12H_2O$ and 5.95 g of anhydrous alanine, $C_3H_7NO_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 31 pieces with an average weight of 2.1 g. The aluminum content was 2.25 mg per gram and alanine content was 39.6 mg per gram. The molar ratio of alanine to aluminum was 8 to 1. The flavor was very pleasant, without unpleasant aftertaste, but with a strongly astringent and persistant mouth-feel, and was not clearly distinguishable from the corresponding glycine-containing product.

EXAMPLE 7

Lemon-Flavored Aluminum Sodium Sulfate Formulation 84.80 g of lemon-flavored hard candy stock was placed in an aluminum pan and heated at 210° F. to a mobile syrup. To this hot stock was added 15.20 g of a dry, finely-ground mixture containing 10.19 g of $AlNa($ SO$_4$)$_2$.12H$_2$O and 5.01 g of anhydrous glycine, C$_2$H$_5$NO$_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.0 cm square. On cooling to room temperature, the squares were easily broken out of the mass. The yield was 81 pieces with an average weight of 1.0 g. The aluminum content was 6.0 mg per gram and glycine content was 50.1 mg per gram. The molar ratio of glycine to aluminum was 3 to 1. The flavor was very pleasant, without unpleasant aftertaste, but with a strongly astringent and persistant mouth-feel.

EXAMPLE 8

Lemon-Flavored Aluminum Acetate Formulation 97.85 g of lemon-flavored hard candy stock was placed in an aluminum pan and heated at 210° F. to a mobile syrup. To this hot stock was added 2.15 g of a dry, finely-ground mixture containing 0.76 g of Al(CH$_3$CO$_2$)$_3$ and 1.39 g of anhydrous glycine, C$_2$H$_5$NO$_2$. The dry component was evenly distributed in the melted stock by thorough mixing and the product was poured onto a greased aluminum pan, forming a circular mass approximately 4 mm thick. As it cooled toward room temperature, it was scored with a lightly greased knife into pieces approximately 1.5 cm square. On cooling to room temperature, the squares were easily broken out of the mass. The yield was 33 pieces with an average weight of 2.4 g. The aluminum content was 1.0 mg per gram and glycine content was 13.9 mg per gram. The molar ratio of glycine to aluminum was 5 to 1. The flavor was very pleasant, without unpleasant aftertaste, and with an astringent mouth-feel.

EXAMPLE 9

Lemon-Flavored Aluminum Chloride Formulation 92.34 g of lemon-flavored hard candy stock, and 7.66 g of a dry, finely-ground mixture containing 1.62 g of AlCl$_3$.6H$_2$O and 6.04 g of anhydrous glycine, C$_2$H$_5$NO$_2$, was ground in a high-speed grinding mill until the entire mixture was reduced to a fine powder. The powder was compressed into lozenge-shaped tablets approximately 1.5×1.0×0.5 cm in size and weighing 3.2 g each. The aluminum content was 1.81 mg per gram and glycine content was 60.4 mg per gram. The molar ratio of glycine to aluminum was 12 to 1. One tablet dissolved in the mouth within 12 minutes. The flavor was very pleasant, without unpleasant aftertaste, but with a strongly astringent and persistant mouth-feel.

It is claimed:

1. A slow-release candy composition for oral consumption comprising a hard candy base material and uniformly contained in said hard candy base material an aluminum compound and an amino acid, said amino acid being capable of forming a complex with said aluminum compound and being selected from the group consisting of glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,l-lysine; said composition containing from about 1 mg to about 10 mg of aluminum for each gram of said composition, and the molar ratio of said amino acid to aluminum being from about 1 to 20; whereby said aluminum is slowly and uniformly released as said composition is being orally consumed.

2. The composition of matter of claim 1 wherein said amino acid is glycine.

3. The composition of matter of claim 1 wherein said aluminum compound is an aluminum compound in the form of a sulfate, chloride hexahydrate, acetate, acetotartrate, ammonium sulfate, carbonate, chlorhydrate, diacetate, hydroxychloride, magnesium silicate, potassium sulfate, sodium sulfate, acetate oxide, gluconate, glucuronate, and ascorbate; dihydroxyaluminum aminoacetate, and hydroxyaluminum di-aminoacetate.

4. The composition of matter of claim 1 wherein the aluminum compound is a complex of trivalent aluminum with said amino acid.

5. The composition of matter of claim 1 wherein the aluminum compound is aluminum chloride hexahydrate.

6. The composition of matter of claim 1 wherein the aluminum compound is aluminum sulfate.

7. The composition of matter of claim 1 wherein the aluminum compound is aluminum sulfate octadecahydrate.

8. The composition of matter of claim 1 wherein the aluminum compound is aluminum acetate.

9. The composition of matter of claim 1 wherein the aluminum compound is aluminum acetotartrate which contains 70% basic aluminum acetate and 30% tartaric acid.

10. The composition of matter of claim 1 wherein the aluminum compound is aluminum ammonium sulfate dodecahydrate.

11. The composition of matter of claim 1 wherein the aluminum compound is aluminum diacetate.

12. The composition of matter of claim 1 wherein the aluminum compound is aluminum hydroxychloride.

13. The composition of matter of claim 1 wherein the aluminum compound is aluminum chlorhydrate.

14. The composition of matter of claim 1 wherein the aluminum compound is aluminum carbonate.

15. The composition of matter of claim 1 wherein the aluminum compound is aluminum magnesium silicate.

16. The composition of matter of claim 1 wherein the aluminum compound is aluminum potassium sulfate dodecahydrate.

17. The composition of matter of claim 1 wherein the aluminum compound is aluminum sodium sulfate dodecahydrate.

18. The composition of matter of claim 1 wherein the aluminum compound is aluminum acetate oxide tetrahydrate.

19. The composition of matter of claim 1 wherein the aluminum compound is aluminum gluconate.

20. The composition of matter of claim 1 wherein the aluminum compound is aluminum glucuronate.

21. The composition of matter of claim 1 wherein the aluminum compound is aluminum ascorbate.

22. The composition of matter of claim 1 wherein the aluminum compound is dihydroxyaluminum aminoacetate.

23. The composition of matter of claim 1 wherein the aluminum compound is hydroxyaluminum di-aminoacetate.

24. The composition of matter of claim 4 wherein said aluminum complex is an aluminum glycine complex having the formula Al(C$_2$H$_4$NO$_2$)$_3$, combined with from 0.3 to 6.0 parts by weight of the anhydrous amino acid glycine, having the formula C$_2$H$_5$NO$_2$.

25. The composition of matter of claim 4 wherein said aluminum complex is an aluminum alanine complex having the formula $Al(C_3H_6NO_2)_3$, combined with from 0.3 to 6.0 parts by weight of the anhydrous amino acid alanine, having the formula $C_3H_7NO_2$.

26. The composition of matter of claim 4 wherein said aluminum complex is an aluminum D,L-lysine complex having the formula $Al(C_3H_6NO_2)_3$, combined with from 0.16 to 3.2 parts by weight of the anhydrous amino acid glycine.

27. The composition of matter of claim 4 wherein said aluminum complex is an aluminum L-leucine complex having the formula $Al(C_6H_{12}NO_2)_3$, combined with from 0.18 to 3.6 parts by weight of the anhydrous amino acid glycine.

28. The composition of matter of claim 4 wherein said aluminum complex is an aluminum D,L-2-aminobutyric acid complex having the formula $Al(C_4H_8NO_2)_3$, combined with from 0.23 to 4.6 parts by weight of the anhydrous amino acid glycine.

29. The composition of matter of claim 4 wherein said aluminum complex is an aluminum L-valine complex having the formula $Al(C_5H_{10}NO_2)_3$, combined with from 0.20 to 4.0 parts by weight of the anhydrous amino acid glycine.

* * * * *